(12) United States Patent
Lin

(10) Patent No.: US 8,720,265 B2
(45) Date of Patent: May 13, 2014

(54) SPRING TESTING FIXTURE AND MEASURING ASSEMBLY THEREOF

(75) Inventor: Jui-pin Lin, New Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 397 days.

(21) Appl. No.: 13/158,381

(22) Filed: Jun. 11, 2011

(65) Prior Publication Data

US 2012/0312091 A1 Dec. 13, 2012

(51) Int. Cl.
*G01L 1/04* (2006.01)
*G01N 3/26* (2006.01)

(52) U.S. Cl.
USPC .............................................. 73/161; 73/756

(58) Field of Classification Search
None
See application file for complete search history.

(56) References Cited

U.S. PATENT DOCUMENTS

| | | | | |
|---|---|---|---|---|
| 3,025,092 A | * | 3/1962 | Weiner | 292/163 |
| 4,967,047 A | * | 10/1990 | Betterton et al. | 200/83 J |
| 5,000,037 A | * | 3/1991 | Baresh | 73/104 |
| 7,966,885 B2 | * | 6/2011 | Bayer et al. | 73/663 |

FOREIGN PATENT DOCUMENTS

JP 02107811 A * 4/1990

* cited by examiner

*Primary Examiner* — Lisa Caputo
*Assistant Examiner* — Jermaine Jenkins
(74) *Attorney, Agent, or Firm* — Cheng-Ju Chiang

(57) ABSTRACT

A spring testing fixture and measuring assembly thereof are described. The spring testing fixture includes a measuring assembly, an upper cover and a lower cover. The measuring assembly further includes a contact plate, a containing space and a buckling unit. The contact plate of the measuring assembly is correspondingly adapted to the configuration (or profile) of the spring for effectively restricting the exerted force on the spring to precisely measure the practical reliability and the life span of the spring.

9 Claims, 10 Drawing Sheets

SPRING TESTING FIXTURE AND MEASURING ASSEMBLY THEREOF

FIELD OF THE INVENTION

The present invention relates to a fixture device, and more particularly relates to a spring testing fixture and measuring assembly thereof

BACKGROUND OF THE INVENTION

With the rapid development of the industrial technology, a variety of electronic products are weeded through the old to bring forth the new. Before the novel products are released, a series of reliability testing and life span testing procedures are performed on the products to ensure the quality of the products. Specifically, a spring is a key component in a vibration system and various types of spring are utilized to different fields system for application requirement. The spring stores the energy quantity by deforming itself and releases the deformation energy when necessary. Thus, the spring is usually used in the mechanical structure of the electronic products. For example, the articles for daily use, mechanical structures, electric appliance, and communications and transportation equipment also utilize the spring.

Referring to FIG. 1, a conventional spring measurement system is used to test the characteristic parameters of the spring. The spring measurement system includes a loading component 2, a supporting base 6 wherein the loading component 2 is connected to the computer system 16 via a signal wire 18. During the test procedure of the spring measurement system, the force from the loading component 2 cannot precisely concentrate on the spring 4 for extending or compressing the spring 4 because an external force is not exerted on the spring 4 to bind the surroundings of the spring. Such the situation makes the characteristic parameters measured by the computer system 16 quite different from these parameters while the spring 4 is installed in the mechanical structure so that the characteristic parameters of the spring 4 cannot be acquired.

Consequently, there is a need to design a novel fixture device to solve the aforementioned problems of the conventional spring measurement system for the reliability testing and life span testing procedures.

SUMMARY OF THE INVENTION

One objective of the present invention is to provide a spring testing fixture and measuring assembly for precisely constructing operation situation of the spring based on the configuration (or profile) of the spring so that the measured characteristic parameters, e.g. reliability and life span, are more accurate.

According to the above objective, the present invention sets forth a spring testing fixture and measuring assembly. The spring testing fixture includes a measuring assembly, an upper cover and a lower cover. The measuring assembly has a roof, a bottom portion and an internal space between the roof and the bottom portion for containing the spring. The upper cover has an opening wherein the roof of the measuring assembly partly exposes outside the opening. The lower cover has a surface area for supporting the bottom portion of the measuring assembly wherein the measuring assembly is disposed between the upper cover and the lower cover. At least one jammed portion is engaged to at least one complementary recess for assembling the upper cover and the lower cover.

In the present invention, the measuring assembly further includes a contact plate, a containing space and a buckling unit. The contact plate has a protrusion portion. The containing space accommodates the spring. The buckling unit has at least one big fastener and at least one small fastener, wherein the big fastener is bent outward from a side-wall of the containing space for withstanding against the inner area of the upper cover and the small fastener is bent inward from the side-wall of the containing space for contacting the contact plate.

The measuring assembly is bound by the upper cover and lower cover therebetween so that the roof of the measuring assembly partly exposes outside the opening of the upper cover. That is, a protrusion portion composed of a semi-sphere formation exposes the upper surface area the contact plate outside the upper cover. Further, the protrusion portion with the semi-sphere formation contacts the loading component. When the contact plate of the measuring assembly directly contacts the loading component, the loading component can exerts the force on the protrusion portion with the semi-sphere formation of the contact plate.

Based on the spring testing fixture of the present invention, when the spring endures the force, the contact plate of the spring testing fixture moves downward, the loading component directly contacts the contact plate and the lower surface area of the protrusion portion of the contact plate is correspondingly adapted to the configuration of the spring. Thus, the force from the loading component is capable of uniformly exerting on the spring so that spring is compressed and deformed down to the bottom of the containing space and the force is transmitted to the surface of the lower cover. The reacting force from the lower cover pushes the bottom of the containing space so that the compressed force of the spring is sent to the loading component upwardly. The loading component transmits the compressed force of the spring to the computer system for processing through the signal wire.

The lower surface area of the protrusion portion of the contact plate is formed according to the configuration of the spring so that the protrusion portion is the same as the aspect of the mechanical structure.

In the present invention, the measuring assembly 1 supports the spring for effectively restricting the exerted force. Such the situation is simulated to be identical to the practical operation of the product for making the measuring data more accurate.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
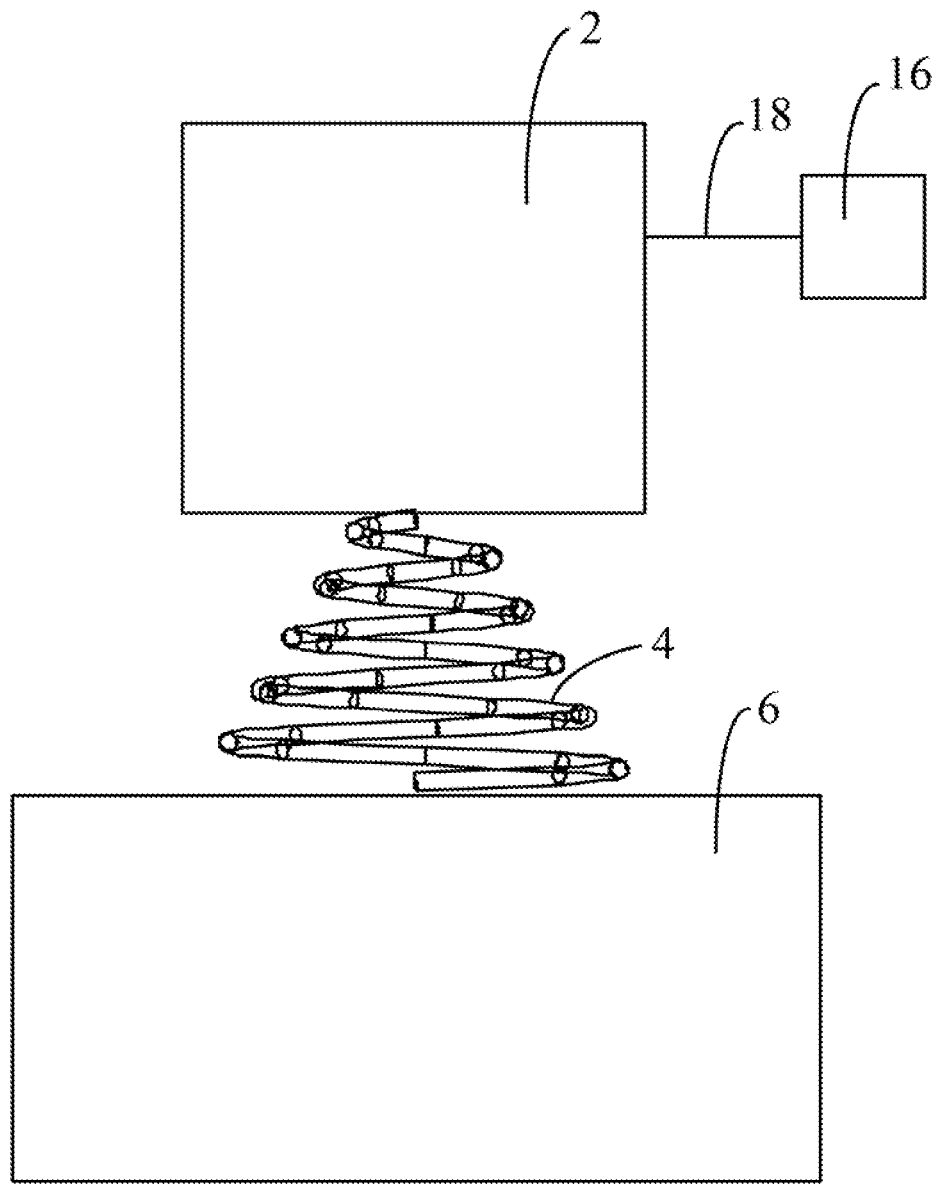
FIG. 1 is a schematic view of a conventional spring measurement system.

In the following description, the same elements will be designated by the same reference numerals although they are shown in different drawings. A face in the accompanying drawings is defined as a normal vector perpendicular to the face. Each of these terminologies is not used to define an essence, order or sequence of a corresponding component but used merely to distinguish the corresponding component from other component(s).

Figure 2:
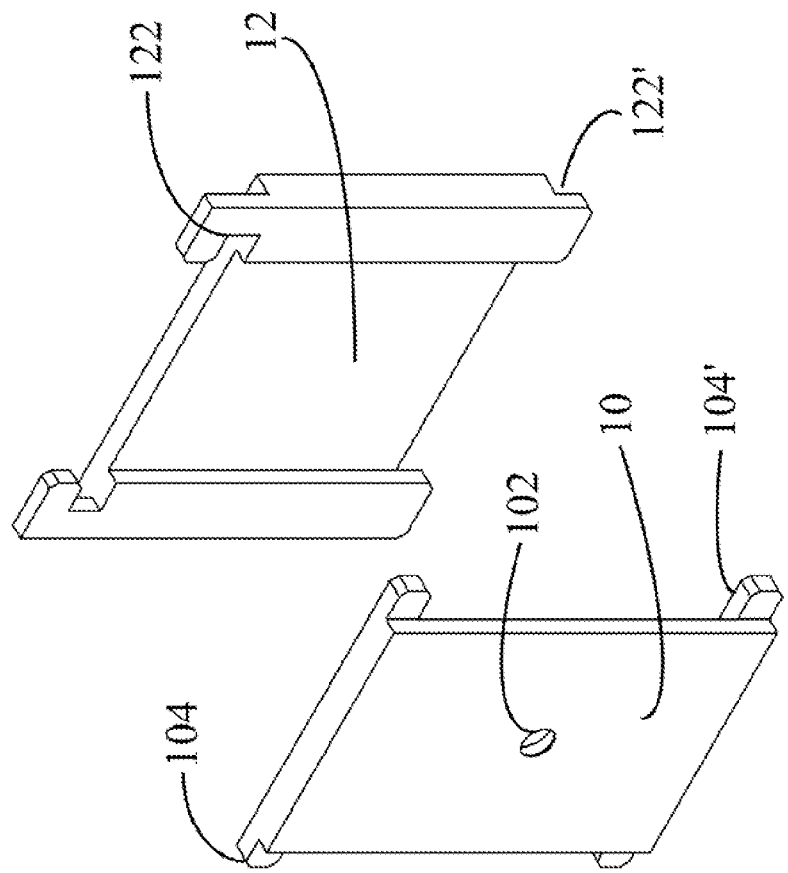
FIG. 2 is a schematic exploded perspective view of a spring testing fixture according to one embodiment of the present invention.
Figure 2:
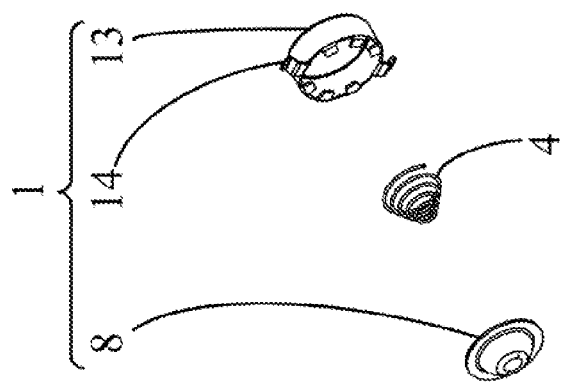

FIG. 2 is a schematic exploded perspective view of a spring testing fixture according to one embodiment of the present invention. The spring testing fixture is employed to test the reliability and life span of a spring 4 and includes a measuring assembly 1, an upper cover 10 and a lower cover 12. The measuring assembly 1 has a roof, a bottom portion and an internal space between the roof and the bottom portion for containing the spring 4. The upper cover 10 has an opening 102 wherein the roof of the measuring assembly 1 partly exposes outside the opening 102. The lower cover 12 further includes a surface area for supporting the bottom portion of the measuring assembly 1. The measuring assembly 1 is disposed between the upper cover 10 and the lower cover 12. The opposite sides of the upper cover 10 and the lower cover 12 respectively form two pairs of complementary jammed portions 104, 104' and recesses 122, 122'. The jammed portions 104, 104' are engaged into the recesses 122, 122' correspondingly for combining the upper cover 10 and the lower cover 12.

Figure 3A:
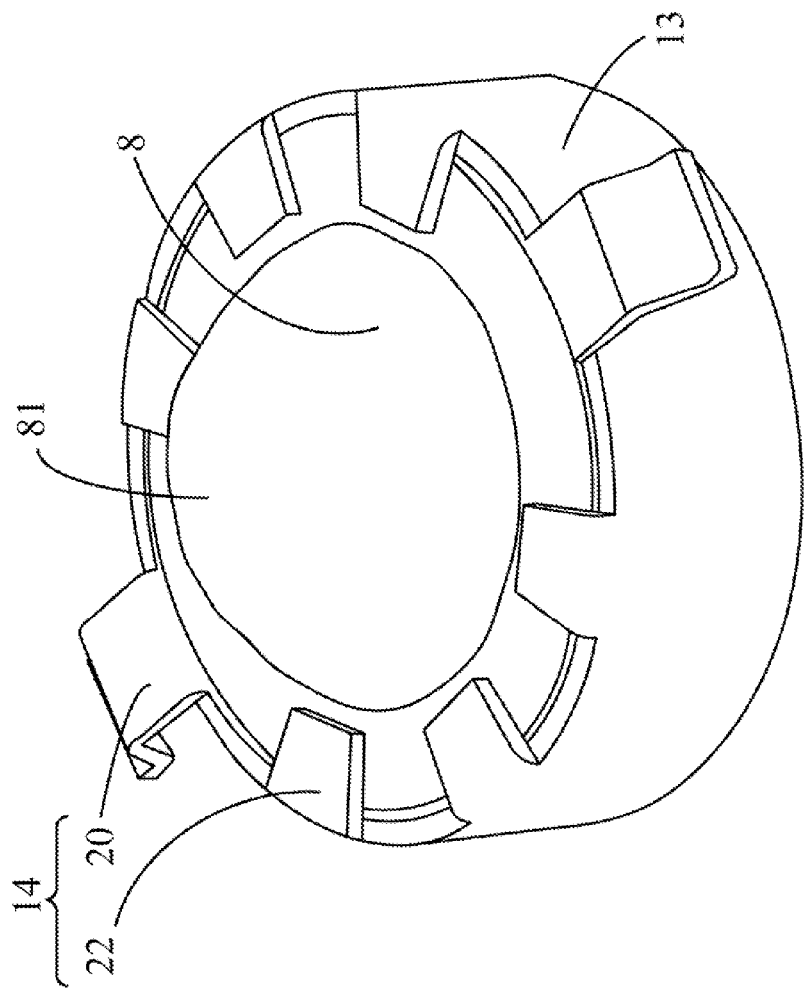
FIG. 3A is a schematic three-dimensional view of a measuring assembly of the spring testing fixture according to one embodiment of the present invention.
Figure 3B:
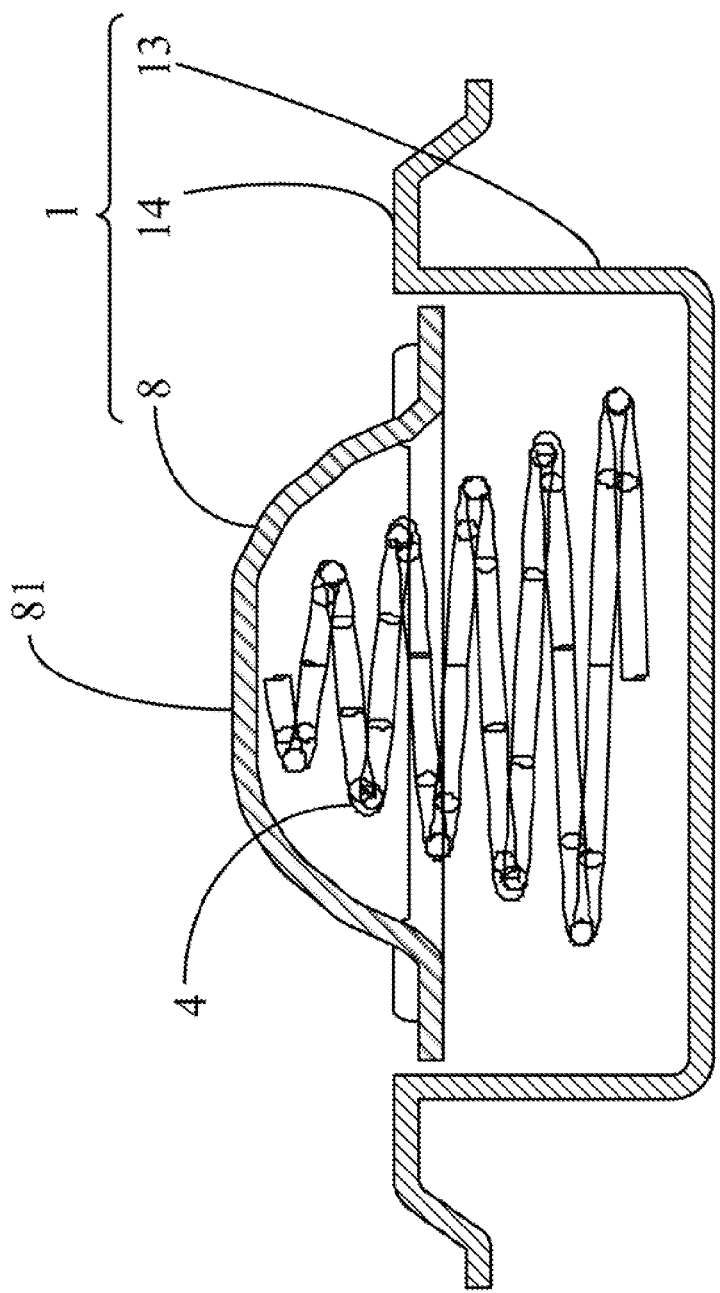
FIG. 3B is a schematic cross-sectional view of a measuring assembly of the spring testing fixture according to one embodiment of the present invention.

FIG. 3A is a schematic three-dimensional view of a measuring assembly 1 of the spring testing fixture according to one embodiment of the present invention. FIG. 3B is a schematic cross-sectional view of a measuring assembly 1 of the spring testing fixture according to one embodiment of the present invention. The measuring assembly 1 containing the spring 4 further includes a contact plate 8, a containing space 13, and a buckling unit 14. The contact plate 8 is disposed on the roof of the measuring assembly 1 and the containing space 13 is disposed on the bottom portion of the measuring assembly 1. In one embodiment, the contact plate 8 is formed by a sphere-like sheet metal, and has an upper surface area and a lower surface area. The upper surface has a protrusion portion 81 composed of a semi-sphere formation and an annular extending plane surrounding the protrusion portion 81. The annular extending plane contacts the at least one small fastener 21 and the spring 4 supports a lower surface area of the protrusion portion 81 of the contact plate 8. The containing space 13 accommodates the spring 4. The buckling unit 14 is formed on the circumferential edge of the vertical side-wall of the containing space 13, and includes a plurality of big fastener 20 and small fastener 21 which are arranged in an alternating manner. The big fastener 20 is bent outward from the vertical side-wall of the containing space 13 for withstanding against the inner area of the lower surface of the upper cover 10. The small fastener 21 is bent inward from the vertical side-wall of the containing space 13 for contacting the upper surface area of the annular extending plane of the contact plate 8.

In FIG. 3B, the lower surface area of the protrusion portion 81 of the contact plate 8 is correspondingly adapted to the configuration of the spring 4 for accurately measuring the characteristic parameters, e.g. reliability or life span, when the spring 4 is installed in the mechanical structure.

FIGS. 4A-4E are schematic steps of assembling the spring testing fixture according to one embodiment of the present invention.

Figure 4A:
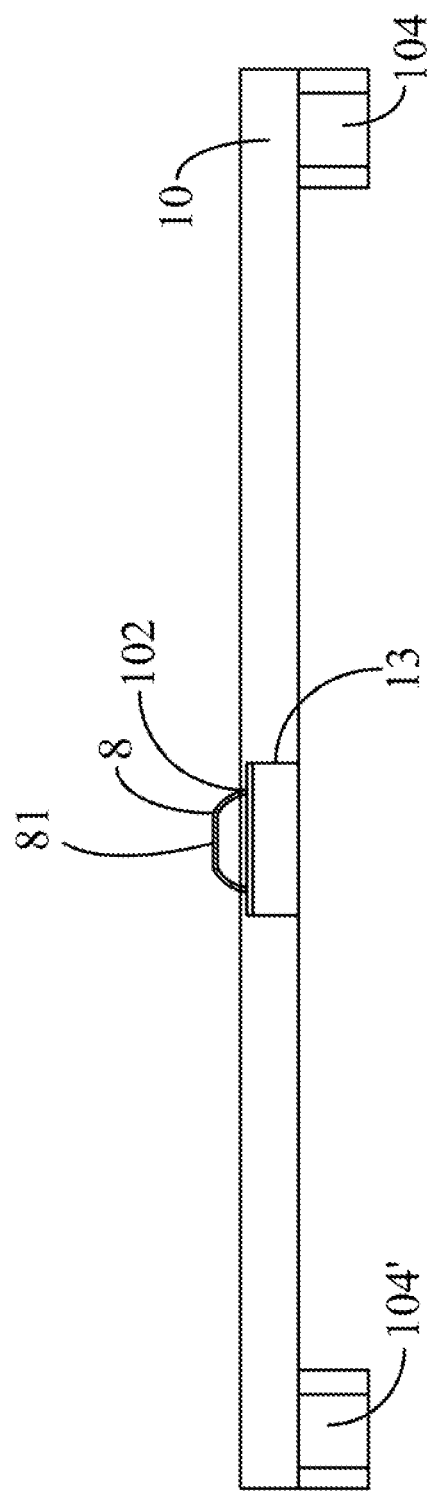
FIGS. 4A-4E are schematic steps of assembling the spring testing fixture according to one embodiment of the present invention.
Figure 4B:
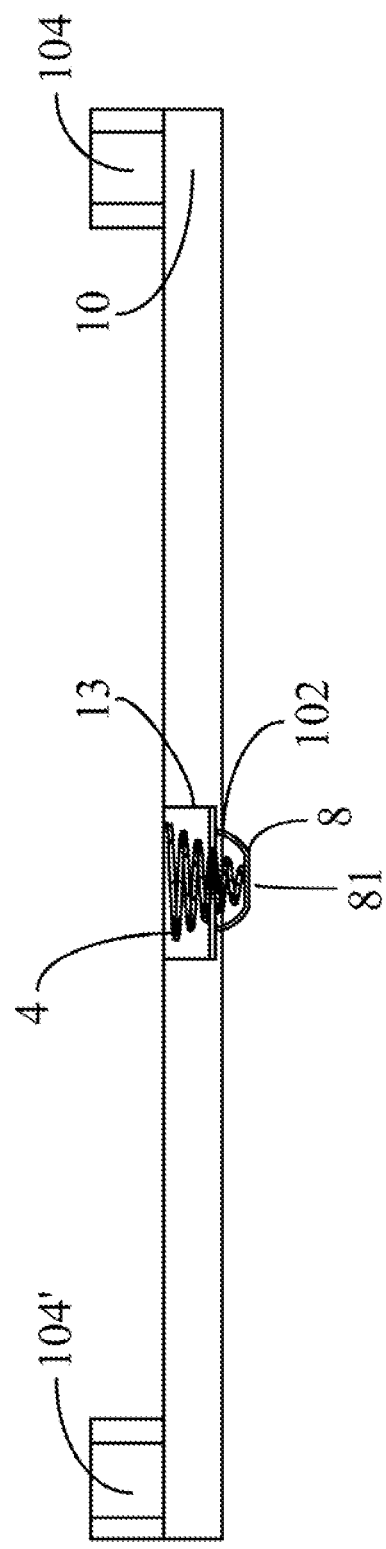
Figure 4C:
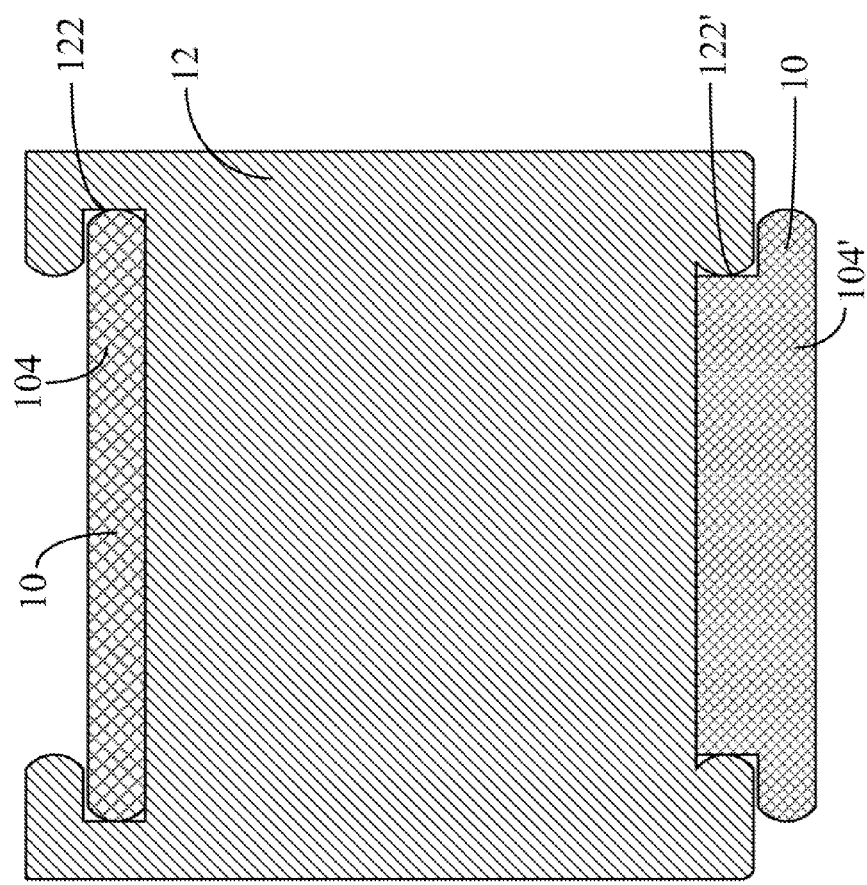
Figure 4D:
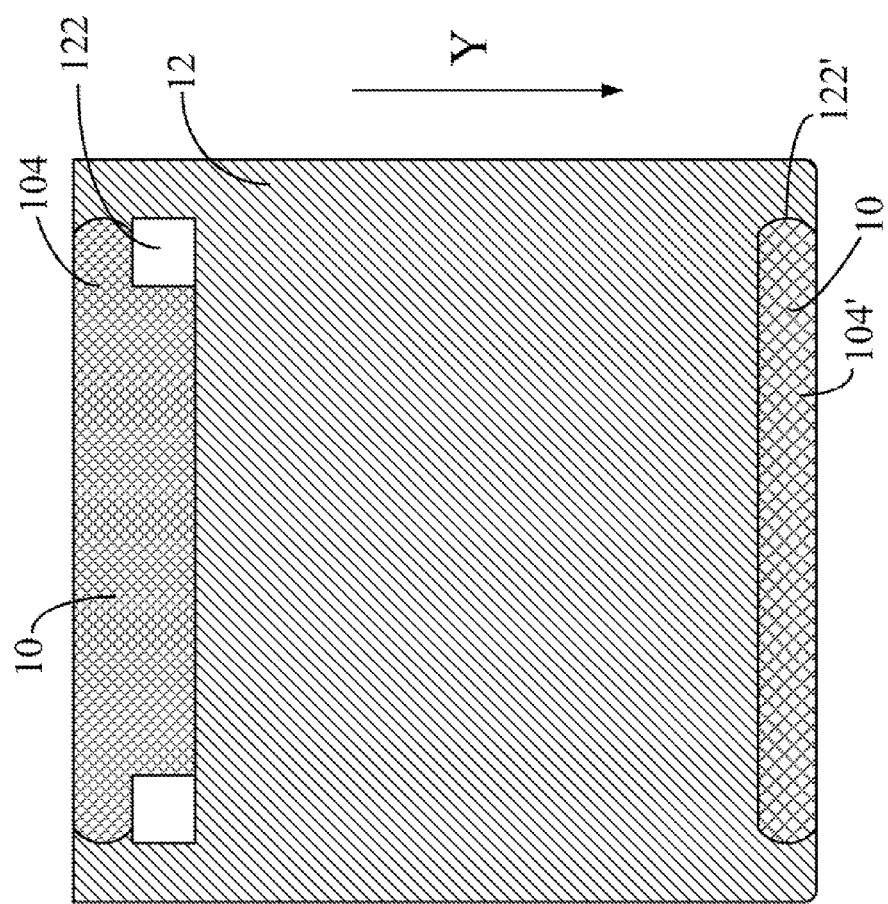
Figure 4E:
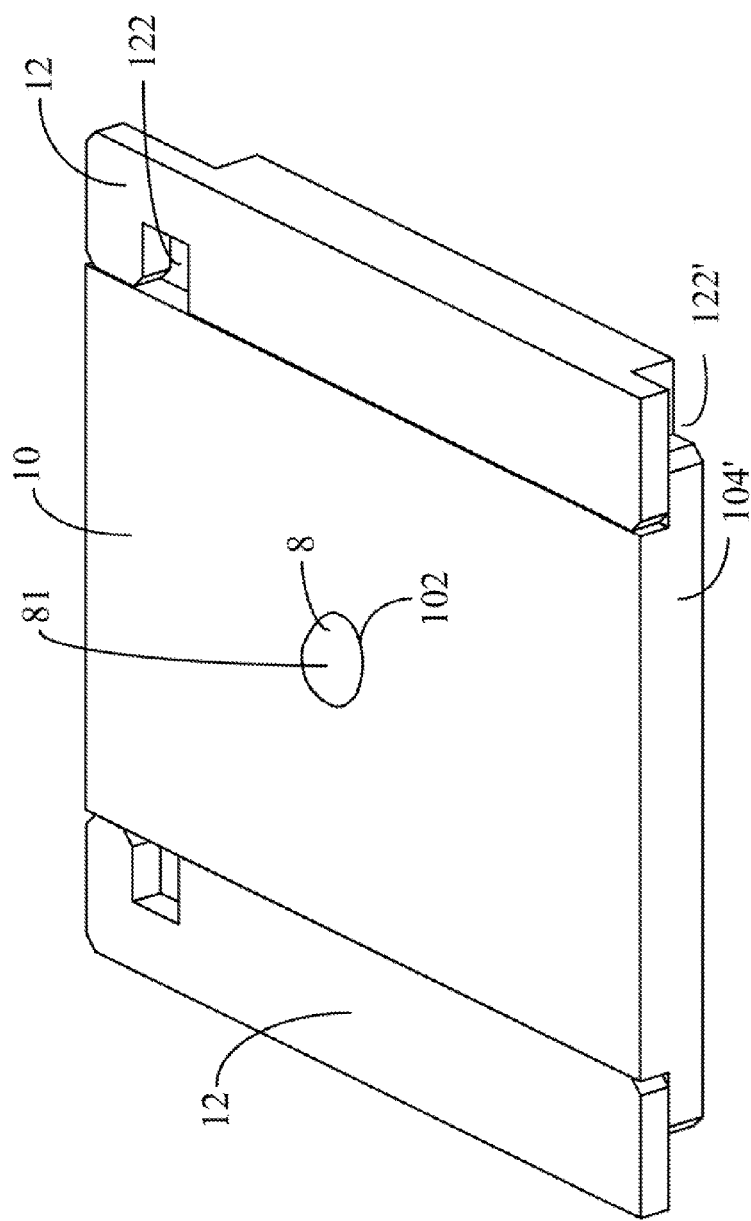

In FIG. 4A, the contact plate 8 and the containing space 13 of he measuring assembly 1 are sequentially placed in the opening 102 of the upper cover 10. In FIG. 4B, after the upper cover 10 is overturned, a spring 4 is put into the containing space 13 of the measuring assembly 1 and contacts the buckling unit 14. Afterwards, in FIG. 4C, the jammed portions 104 of the upper cover 10 are engaged into the recesses 122 of the lower cover 12 for combining the lower cover 12 with the upper cover 10 thereon. Finally, in FIG. 4D, the lower cover 12 moves along the direction Y with respect to the upper cover 10 until the jammed portions 104' of the upper cover 10 are engaged into the recesses 122' of the lower cover 12 so that the lower cover 12 and the upper cover 10 are combined together to construct the spring testing fixture. That is, at least one jammed portion 104, 104' is engaged to at least one recess 122, 122' for assembling the upper cover 10 and the lower cover 12. FIG. 4E depicts an assembly view of the spring testing fixture.

Figure 5:
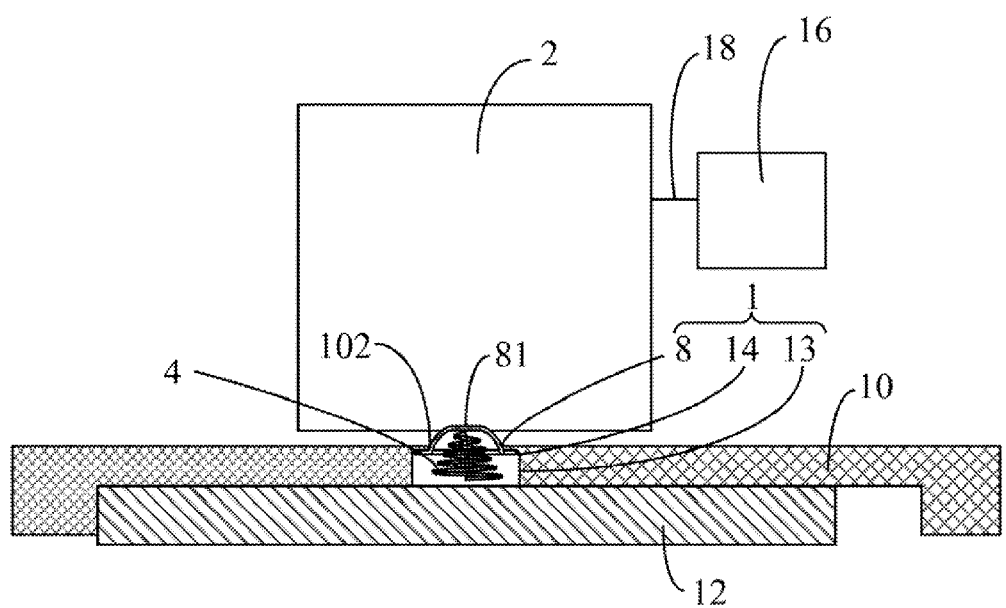
FIG. 5 is a schematic view of the spring testing fixture of spring measurement system according to one embodiment of the present invention.

FIG. 5 is a schematic view of the spring testing fixture of spring measurement system according to one embodiment of the present invention. The spring measurement system includes a measuring assembly 1, an upper cover 10, a lower cover 12, loading component 2 and a computer system 16 wherein the loading component 2 is connected to the computer system 16 via a signal wire 18. The measuring assembly 1 further includes a contact plate 8, a containing space 13, and a buckling unit 14. It should be noted that the loading component 2 directly contacts the contact plate 8 and the lower surface area of the protrusion portion 81 of the contact plate 8 is correspondingly adapted to the configuration of the spring 4. Thus, the force from the loading component 2 is capable of uniformly exerting on the spring 4 so that spring 4 is compressed and deformed down to the bottom of the containing space 13 and the force is transmitted to the surface of the lower cover 12. The reacting force from the lower cover 12 pushes the bottom of the containing space 13 so that the compressed force of the spring 4 is sent to the loading component 2 upwardly. The loading component 2 transmits the compressed force of the spring 4 to the computer system 16 for processing through the signal wire 18. Therefore, the parameter of the spring 4 can be precisely acquired for accurately calculating the characteristic parameter, e.g. reliability and life span, of the spring 4. In one embodiment, the lower surface area of the protrusion portion 81 of the contact plate 8 is formed according to the configuration of the spring 4 so that the protrusion portion 81 is the same as the aspect of the mechanical structure. In the present invention, the measuring assembly 1 supports the spring 4 for effectively restricting the exerted force to move either upward or downward but not to laterally bend. Such the situation is simulated to be identical to the practical operation of the product for making the measuring data more accurate.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A spring testing fixture for testing a spring, the spring testing fixture comprising:
   a measuring assembly having a roof, a bottom portion and an internal space between the roof and the bottom portion for containing the spring, wherein the measuring assembly further comprises:
      a containing space disposed on the bottom portion of the measuring assembly for accommodating the spring; and
      a buckling unit having at least one big fastener, wherein the big fastener is bent outward from a side-wall of the containing space for withstanding against the inner area of the upper cover;
   an upper cover having an opening wherein the roof of the measuring assembly partly exposes outside the opening; and
   a lower cover having a surface area for supporting the bottom portion of the measuring assembly wherein the measuring assembly is disposed between the upper cover and the lower cover.

2. The spring testing fixture of claim 1, wherein the measuring assembly further comprises:
   a contact plate disposed on the roof of the measuring assembly and having a protrusion portion; and
   the buckling unit further having at least one small fastener, wherein the small fastener is bent inward from the side-wall of the containing space for contacting the contact plate.

3. The spring testing fixture of claim 2, wherein the protrusion portion of the contact plate is correspondingly adapted to a configuration of the spring.

4. The spring testing fixture of claim 2, wherein the buckling unit contacts a surface area of the contact plate and an inner area of the upper cover respectively.

5. The spring testing fixture of claim 2, wherein the material of the contact plate is metal.

6. The spring testing fixture of claim 1, wherein at least one jammed portion is engaged to at least one recess for assembling the upper cover and the lower cover.

7. A measuring assembly, comprising:
   a contact plate, having a protrusion portion;
   a containing space, accommodating the spring; and
   a buckling unit having at least one big fastener and at least one small fastener, wherein the big fastener is bent outward from a side-wall of the containing space for withstanding against the inner area of the upper cover and the small fastener is bent inward from the side-wall of the containing space for contacting the contact plate.

8. The measuring assembly of claim 7, wherein the contact plate further comprises an annular extending plane for surrounding the protrusion portion and the annular extending plane contacts the at least one small fastener.

9. The measuring assembly of claim 7, wherein the spring supports a lower surface area of the protrusion portion of the contact plate.

* * * * *